US010927149B2

(12) United States Patent
Goel et al.

(10) Patent No.: US 10,927,149 B2
(45) Date of Patent: Feb. 23, 2021

(54) INDUSTRIALLY SCALABLE PROCESS FOR RECOVERING BIOLOGICALLY ACTIVE RECOMBINANT CARRIER PROTEINS

(71) Applicant: BIOLOGICAL E LIMITED, Telangana (IN)

(72) Inventors: Akshay Goel, Hyderabad (IN); Tushar Joglekar, Hyderabad (IN); Krishnanand Tiwari, Hyderabad (IN); Yogesh Mishra, Hyderabad (IN); Narender Dev Mantena, Hyderabad (IN); Mahima Datla, Hyderabad (IN)

(73) Assignee: Biological E Limited

( * ) Notice: Subject to any disclaimer, the term of this patent is extended or adjusted under 35 U.S.C. 154(b) by 38 days.

(21) Appl. No.: 15/773,381

(22) PCT Filed: Oct. 26, 2016

(86) PCT No.: PCT/IN2016/000262
§ 371 (c)(1),
(2) Date: May 3, 2018

(87) PCT Pub. No.: WO2017/081700
PCT Pub. Date: May 18, 2017

(65) Prior Publication Data

US 2018/0327457 A1 Nov. 15, 2018

(30) Foreign Application Priority Data

Nov. 9, 2015 (IN) ........................... 6037/CHE/2015

(51) Int. Cl.

| | |
|---|---|
| ***A61K 39/00*** | (2006.01) |
| ***C12N 15/70*** | (2006.01) |
| ***C07K 1/18*** | (2006.01) |
| ***C07K 14/005*** | (2006.01) |
| ***C07K 1/113*** | (2006.01) |
| ***C07K 14/195*** | (2006.01) |
| *C07K 1/12* | (2006.01) |
| *C07K 14/22* | (2006.01) |

(52) U.S. Cl.
CPC .......... *C07K 14/005* (2013.01); *C07K 1/1136* (2013.01); *C07K 1/18* (2013.01); *C07K 14/195* (2013.01); *C07K 1/122* (2013.01); *C07K 14/22* (2013.01); *C12N 15/70* (2013.01)

(58) Field of Classification Search
CPC ........ A61K 39/00; A61K 39/02; A61K 39/04; C12N 15/70; C07K 1/18; C07K 1/22
USPC ..................... 424/184.1, 234.1, 278.1, 282.1
See application file for complete search history.

(56) References Cited

U.S. PATENT DOCUMENTS

| | | | |
|---|---|---|---|
| 4,961,969 | A | 10/1990 | Hershenson et al. |
| 2007/0027305 | A1 | 2/2007 | St. John et al. |
| 2015/0133636 | A1 | 5/2015 | Xenopoulos et al. |

FOREIGN PATENT DOCUMENTS

| | | |
|---|---|---|
| EP | 1845103 | 10/2007 |
| WO | WO 2007/016272 | 2/2007 |
| WO | WO 2014/126884 | 8/2014 |

OTHER PUBLICATIONS

Baneyx F., "Recombinant protein expression in *Escherichia coli*," Curr Opin Biotechnol 10(5):411-21 (publication date: Oct. 1999) (Abstract only).
Eiberle et al. "Technical refolding of proteins: Do we have freedom to operate?" Biotechnology Journal 5(6):547-559 (publication date: Jun. 2010) (Abstract only).
Hamada H. et al., "Effect of additives on protein aggregation," Curr Pharm Biotechnol 10(4):400-7 (publication date: Jun. 2009) (Abstract only).
International Search Report and Written Opinion for International Application No. PCT/IN2016/000262 dated Feb. 17, 2017.
Peternel S. "Bacterial cell disruption: a crucial step in protein production," N Biotechnol 30(2):250-4 (publication date: Jan. 25, 2013, epublication date: Oct. 1, 2011) (Abstract only).
Singh et al. "Protein recovery from inclusion bodies of *Escherichia coli* using mild solubilization process," Microbial Cell Factories 14(1):41 (publication date: Mar. 25, 2015).
Singh SM et al., "Solubilization and refolding of bacterial inclusion body proteins," J Biosci Bioeng 99(4):303-10 (publication date: Apr. 2005) (Abstract only).
Stefan et al., "Overexpression and purification of the recombinant diphtheria toxin variant CRM197 in *Escherichia coli*," J Biotechnol 156(4):245-52 (publication date: Dec. 20, 2011, epublication date: Aug. 25, 2011).
Surinder et al. "Solubilization at high pH results in improved recovery of proteins from inclusion bodies of *E. coli*," Journal of Chemical Technology and Biotechnology 83(8):1126-1134 (publication date: Apr. 4, 2008).
Uchida et al., "Diphtheria Toxin and Related Proteins. I. Isolation and Properties of Mutant Proteins Serologically Related to Diphtheria Toxin," The Journal of Biological Chemistry, 248(11):3838-44 (publication date: Jun. 10, 1973).

*Primary Examiner* — Rodney P Swartz
(74) *Attorney, Agent, or Firm* — Perkins Coie LLP

(57) ABSTRACT

The present invention relates to a preparation method which is performed by expressing the recombinant carrier proteins in *Escherichia coli* and purification thereof. More particular, the invention relates to industrially scalable process for the recovery of recombinant carrier proteins.

11 Claims, 4 Drawing Sheets

INDUSTRIALLY SCALABLE PROCESS FOR RECOVERING BIOLOGICALLY ACTIVE RECOMBINANT CARRIER PROTEINS

FIELD OF THE INVENTION

The present invention relates to a preparation method which is performed by expressing the recombinant carrier proteins in *Escherichia coli* and purification thereof. More particular, the invention relates to industrially scalable process for the recovery of recombinant carrier proteins.

BACKGROUND OF THE INVENTION

The role of the carrier protein is to enhance immunogenicity by providing T-cell epitopes via MHC Class II presentation to T-helper cells. Carrier proteins also increase the magnitude of the immune response as well as engender B-cell 'memory'. The number of carrier proteins used in licensed vaccines is relatively limited, which include tetanus toxoid (TT), diphtheria toxoid (DT), Cross Reactive Material 197 ($CRM_{197}$), *Haemophilus influenzae* protein D, *Neisseria* outer membrane protein, Pertussis toxin (PT), Pertactin (PRN) and Filamentous Hemagglutinin (FHA). Access to clinically-proven, safe and efficacious carrier proteins is critical for research in the field of conjugate vaccines. Thus, purification of native, soluble and functional form of carrier proteins is very important and crucial step in conjugate vaccine production.

Absence of toxicity and strong immunogenicity makes carrier proteins such as tetanus toxoid (TT), diphtheria toxoid (DT), Cross Reactive Material 197 ($CRM_{197}$), *Haemophilus influenzae* protein D, *Neisseria* outer membrane protein, Pertussis toxin (PT), Pertactin (PRN) and Filamentous Hemagglutinin (FHA), a robust candidate as a carrier for poor immunogens like peptides, oligosaccharides, polysaccharides and even nucleic acids. Since the said carrier proteins are well characterized hence they are preferred over other carrier proteins and therefore widely used in commercially available vaccines.

$CRM_{197}$, a mutant form of DT was isolated in the early 1970's. It also contributed to the understanding of the A and B chain structure and function of DT. Uchida et al., *The Journal of Biological Chemistry,* 248(11):3838-44 (publication date: Jun. 10, 1973) described the isolation and properties of several mutants including $CRM_{197}$. $CRM_{197}$ is a non-toxic DT mutant that contains a lesion in the A chain which blocks ADP-ribosylation. $CRM_{197}$ results from a single base change in the structural gene resulting in the substitution of glutamic acid for glycine at position 52. It is a single polypeptide consisting of 535 amino acids and on SDS gels this protein migrates as a single major band of approximate molecular weight of 58.4 Kda. While $CRM_{197}$ shows no enzymatic activity (except endonuclease), it is immunologically indistinguishable from DT. $CRM_{197}$ has the advantage of being a well-defined protein in contrast to formaldehyde treated toxin (toxoid) which is non-specifically cross linked and subject to rearrangement.

Although *Escherichia coli* is one of the most widely used hosts for the production of recombinant proteins, insoluble expression of heterologous proteins is a major bottleneck in production of these recombinant proteins. A major pathway of product loss during the refolding step is aggregation. These insoluble protein aggregates or inclusion bodies (IB's) can be used only after refolding in vitro into soluble form having its native conformation. The inclusion bodies of different proteins have different characteristics and require a lot of optimization for refolding individual protein. In most cases, a significant amount of precipitation is observed while refolding the proteins. This results in a great loss of overall yield of the target proteins, with approximately 40% being refolded to soluble and biologically active form. Several approaches have been described for in vitro refolding; most of them involve the use of additives for assisting correct folding. These additives or co-solutes play a major role in refolding process and can be classified according to their function as aggregation suppressors or folding enhancers.

U.S. Pat. No. 4,961,969 disclosed an approved procedure for the purification and renaturation of biologically active, bacterially produced IFN-β is described. The partially purified material obtained by solubilization of isolated refractile bodies from the recombinant cells is treated to obtain reduction of the protein in the presence of a chaotropic environment and then oxidized after removal of the reducing agent. However, the chaotropic environment is retained during the oxidation. Upon removal of the chaotropic environment, a solubilizing additive is supplied to maintain the IFN-β in solution. Further purification by conventional means may also be effected.

US patent publication No. 2007/0027305 describes a method of recovering a refolded protein such as Interferon β, which involves solubilizing inclusion bodies (IBs) with chaotropic reagents such as 6M guanidine-hydrochloride (GuHCL) or 8M urea, static mixing a concentrated solution of a denatured protein with a refolding diluent to obtain the refolded protein.

US patent publication No. 2015/0133636 describes a processes for purifying a target molecule from a sample comprising the steps of: (a) providing a sample comprising the target molecule and one or more impurities; (b) adding at least one precipitant to the sample and removing one or more impurities, thereby to recover a clarified sample; (c) subjecting the clarified sample from step (b) to a bind and elute chromatography step comprising at least two separation units, thereby to obtain an eluate comprising the target molecule; and (d) subjecting the eluate to flow-through purification comprising use of two or more media; where at least two steps are performed concurrently for at least a duration of their portion, and wherein the process comprises a single bind and elute chromatography step. It is further disclosed that the process comprises a virus inactivation step between steps (c) and (d) above, using use of one or more in-line static mixers.

The above methods disclosed recovery of proteins, however, there is no specific method disclosed for carrier proteins such as tetanus toxoid (TT), diphtheria toxoid (DT), Cross Reactive Material 197 ($CRM_{197}$), *Haemophilus influenzae* protein D, *Neisseria* outer membrane protein, Pertussis toxin (PT), Pertactin (PRN) and Filamentous Hemagglutinin (FHA). Thus an appropriate method is required which minimizes the loss with improved purity during the refolding step in preparation of carrier proteins.

Objective of the Invention

It is the objective of the present invention to provide an industrially scalable process for the preparation of carrier proteins selected from tetanus toxoid (TT), diphtheria toxoid (DT), Cross Reactive Material 197 ($CRM_{197}$), *Haemophilus influenzae* protein D, *Neisseria* outer membrane protein, Pertussis toxin (PT), Pertactin (PRN) and Filamentous Hemagglutinin (FHA) which are useful in the preparation of vaccine.

Yet another objective of the present invention is to provide an improved method suitable for large-scale production of carrier proteins selected from tetanus toxoid (TT), diphtheria toxoid (DT), Cross Reactive Material 197 ($CRM_{197}$), *Haemophilus influenzae* protein D, *Neisseria* outer membrane protein, Pertussis toxin (PT), Pertactin (PRN) and Filamentous Hemagglutinin (FHA) which is simple with low cost and high yield.

SUMMARY OF THE INVENTION

The present invention provides an industrially scalable method for the preparation of carrier proteins selected from tetanus toxoid (TT), diphtheria toxoid (DT), Cross Reactive Material 197 ($CRM_{197}$), *Haemophilus influenzae* protein D, *Neisseria* outer membrane protein, Pertussis toxin (PT), Pertactin (PRN) and filamentous hemagglutinin (FHA) and the like, which comprises the steps of:

a) transformation of *Escherichia coli* with the desired gene coding for the carrier protein using a plasmid vector,
b) culturing the transformed *Escherichia coli* in suitable culture medium under suitable conditions,
c) isolation and purification of Inclusion bodies,
d) denaturation and solubilization of inclusion bodies at high pH value ranging from 9 to 14,
e) followed by pH adjustment within a range of 6 to 8.5, preferably at 8 of the solubilized protein using in-line static mixer for a period of 0.1 to 200 msec, to produce refolded protein,
f) intermediate purification of the refolded protein using ion exchange chromatography to obtain >90% pure and native carrier protein and
g) the semi purified protein obtained in step (f) is further purified by one or more chromatographic separations using anion exchange chromatography, hydrophobic interaction chromatography, metal & dye affinity chromatography, affinity chromatography, multimodal chromatography, hydroxyapatite chromatography and size exclusion chromatography to obtain purified carrier protein.

The present invention provides an industrially scalable method for the preparation of Cross Reactive Material 197 ($CRM_{197}$) which comprises the steps of:

a) transformation of *Escherichia coli* with the gene coding for $CRM_{197}$ using a plasmid vector,
b) culturing the transformed *Escherichia coli* in suitable culture medium under suitable conditions,
c) isolation and purification of Inclusion bodies,
d) denaturation and solubilization of inclusion bodies at high pH value ranging from 9 to 14,
e) followed by pH adjustment within a range of 6 to 8.5, preferably at 8 of the solubilized protein using in-line static mixer for a period of 0.1 to 200 msec, to produce refolded protein,
f) intermediate purification of the refolded protein using ion exchange chromatography to obtain >90% pure and native $CRM_{197}$ and
g) the semi purified $CRM_{197}$ obtained in step (f) is further purified by one or more chromatographic separations using anion exchange chromatography, hydrophobic interaction chromatography, metal & dye affinity chromatography, affinity chromatography, multimodal chromatography, hydroxyapatite chromatography and size exclusion chromatography to obtain purified $CRM_{197}$.

DETAILED DESCRIPTION OF THE INVENTION

Figure 1:
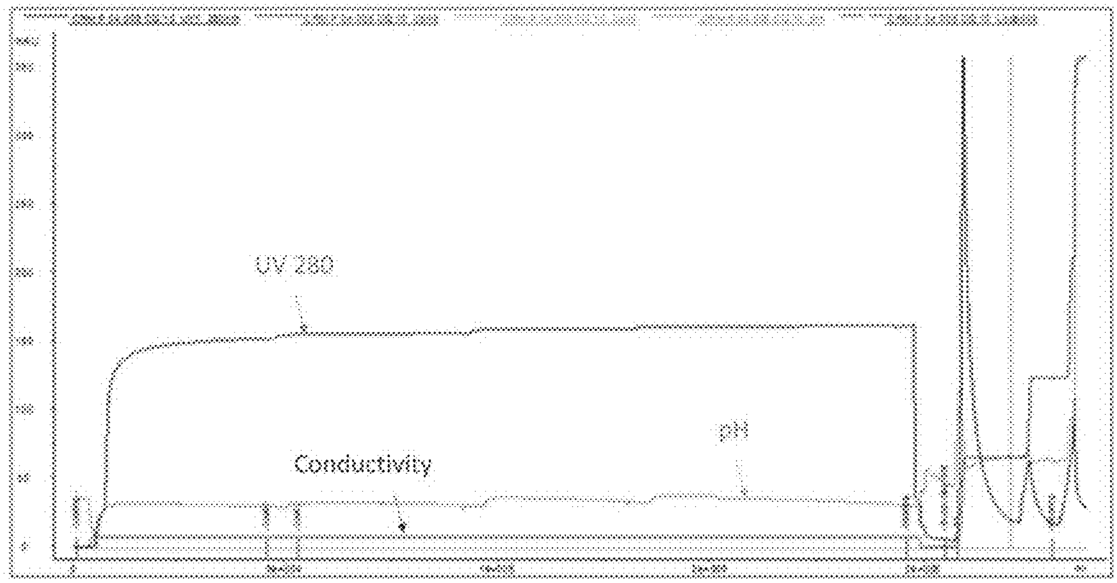
FIG. 1: Ion Exchange chromatogram wherein refolded protein sample was loaded on first anion exchange resin at the flow rate of 150-300 cm per hour. Flow—through and equilibration wash consists of aggregates and other cellular impurities. Elution step is performed to recover refolded target followed by column regeneration. This chromatography is used as capture chromatography, wherein Y-axis represents absorbance at 280 (mAU) and X-axis represents retention volume (ml).

The present invention relates to an industrially scalable process for the preparation of carrier proteins selected from but are not limited to tetanus toxoid (TT), diphtheria toxoid (DT), Cross Reactive Material 197 ($CRM_{197}$), *Haemophilus influenzae* protein D, *Neisseria* outer membrane protein, Pertussis toxin (PT), Pertactin (PRN) and filamentous hemagglutinin (FHA) in a prokaryotic host wherein the target protein is expressed as inclusion bodies in *Escherichia coli*, inclusion bodies are isolated and purified and the purified inclusion bodies are denatured followed by refolding. Further purification is performed using chromatographic separation to obtain pure and native carrier proteins.

*Escherichia coli* strain used is selected from but not limited to BL21DE3, Origami2, BL21A1, W3110, HMS174, C43, ER2566, MAX, B834.

Inclusion bodies are refractile, intracellular protein aggregates usually observed in bacteria upon targeted gene overexpression. In general solubilisation agents and refolding buffers are used are for solubilizing the inclusion bodies and refolding of the protein, wherein the solubilisation agent is removed during refolding. Protein refolding from denatured proteins is influenced by several factors, including solubility of protein, removal of denaturant, and assistance of refolding by co-solute or additives.

Chaotropic agents are cosolutes that can disrupt the hydrogen bonding network between water molecules and reduce the stability of the native state of proteins by weakening the hydrophobic effect. Hence in the present invention solubilisation of inclusion bodies are being carried out at high pH value ranging from 8 to 14 without the use of chaotropic agent which are associated with challenges like they are corrosive, risk of powder handling in graded area, disposal and waste management and impact on protein integrity (carbamylation).

The solubilizing of inclusion bodies is carried out using buffers selected from carbonate, bicarbonate, Tris, borate, Glycine and NaOH, preferably Tris buffer. The concentration used during the solubilisation of inclusion bodies (IBs) may range from 50 to 200 mM.

The present invention also provides a process for the preparation of carrier proteins wherein the refolding step has been optimized using in-line static mixer by rapid pH adjustment without using refolding buffers for a period of 0.1 to 200 microseconds.

Accordingly, the main embodiment of the invention provides cost effective, robust, industrial scale chromatography based process for preparation of recombinant carrier proteins selected from tetanus toxoid (TT), diphtheria toxoid (DT), Cross Reactive Material 197 ($CRM_{197}$), *Haemophilus influenzae* protein D, *Neisseria* outer membrane protein, Pertussis toxin (PT), Pertactin (PRN) and Filamentous Hemagglutinin (FHA) from a prokaryotic expression system, wherein protein is expressed as inclusion bodies which comprises:

a. transformation of bacterial cells with the desired gene coding for carrier proteins using a plasmid vector,
b. culturing the transformed bacterial cells in chemically defined media supplemented with glucose as carbon source wherein pH is maintained at 5-9 and at temperature of 20-40° C.;
c. lysing bacterial cells by mechanical means above 800-1200 bars thereby producing a lysate containing inclusion bodies and cellular components;
d. clarifying the aqueous cell lysate by separating solids from the solution;
e. isolation and purification of inclusion bodies (IBs) by using buffers selected from carbonate, bicarbonate, Tris, borate, Glycine and NaOH to remove cellular contaminants to form a pellet of purified IBs;
f. denaturation and solubilization of inclusion bodies (IBs) at high pH value ranging from 9 to 14 using buffers selected from carbonate, bicarbonate, Tris, borate, Glycine and NaOH buffer;
g. rapid pH adjustment within a range of 6 to 8.5, preferably at 8 of solubilized carrier proteins using acid containing redox systems and inline static mixer for a period of 0.1 to 200 msec, to produce refolded protein,
h. intermediate purification of the refolded protein using ion exchange chromatography to obtain >90% pure and native carrier protein and
i. the semi purified protein obtained in step (h) is further purified by one or more chromatographic separations using anion exchange chromatography, hydrophobic interaction chromatography, metal & dye affinity chromatography, affinity chromatography, multimodal chromatography, hydroxyapatite chromatography and size exclusion chromatography to obtain to obtain purified carrier protein.

Rapid pH adjustment of solubilized carrier proteins is carried out using organic or inorganic acids like HCl, orthophosphoric acid, acetic acid, citric acid containing redox system like cysteine and cysteine, using inline static mixer thus affecting refolding; wherein the purified inclusion bodies are denatured followed by pH adjustment of the solubilized protein using in-line static mixer for a period of 0.1 to 200 msec, to produce refolded protein.

In a preferred embodiment, HCl is used for rapid pH adjustment during refolding step (g) and the concentration may range from 100 to 500 mM HCl and cysteine may range from 2 to 20 M and cysteine from 1 to 10 M.

In an embodiment of the present invention, the refolding step is carried out using static mixer by rapid pH adjustment within a range of 6 to 8.5, preferably at 8 in microseconds wherein pH being the most critical factor having no significant influence on the target protein concentration during refolding.

The refolding may be performed at a temperature in the range to 2 to 10° C., preferably, at 4° C. The dilution ratio of the HCl and inclusion bodies may be kept constant or the dilution ratio may be selected from 0 to 5:1 to 5.

In an embodiment of the present invention, use of low dilution in the pH range of 6 to 8.5 during the refolding step is carried out which gives major advantages in the facility requirement and hence makes the process economical.

In another embodiment, the purified inclusion bodies was renatured followed by pH adjustment of the solubilized protein using in-line static mixer for a period of 0.1 to 200 msec, to produce refolded protein. The above mentioned inclusion bodies was solubilized in 100 mM Tris buffer. The pH of the solubilized inclusion bodies was adjusted to 8 by 300 mM HCl containing 2 to 20 mM cysteine & 1 to 10 mM cysteine. The temperature of all the solutions is maintained between 0-6° C.

The purified $CRM_{197}$ prepared according to the present invention meets all the specifications as laid in Table I below.

TABLE I

Figure 4:
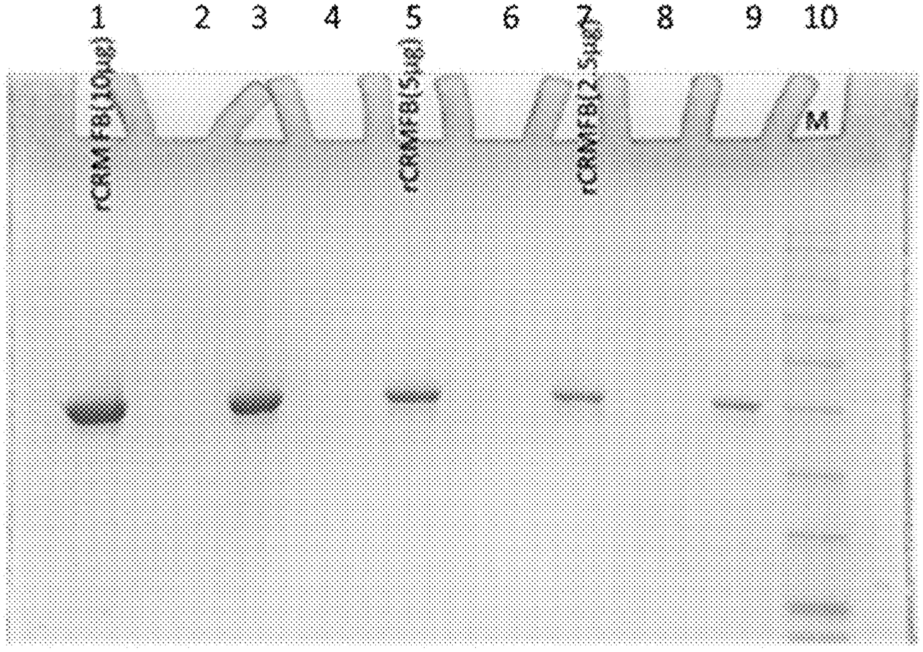
FIG. 4: SDS—Reducing SDS—PAGE analysis was performed to check purity and nicking by loading various amount of purified $rCRM_{197}$ wherein Lane 8, 6, 4 and are blank. Lane 1, 3, 5, 7, and 9 are loaded with purified $rCRM_{197}$ with increasing concentrations (2.5 μg, 5 μg, 7.5 μg & 10 μg). Protein low molecular weight marker (BioRad) was loaded in Lane 10.
Figure 5:
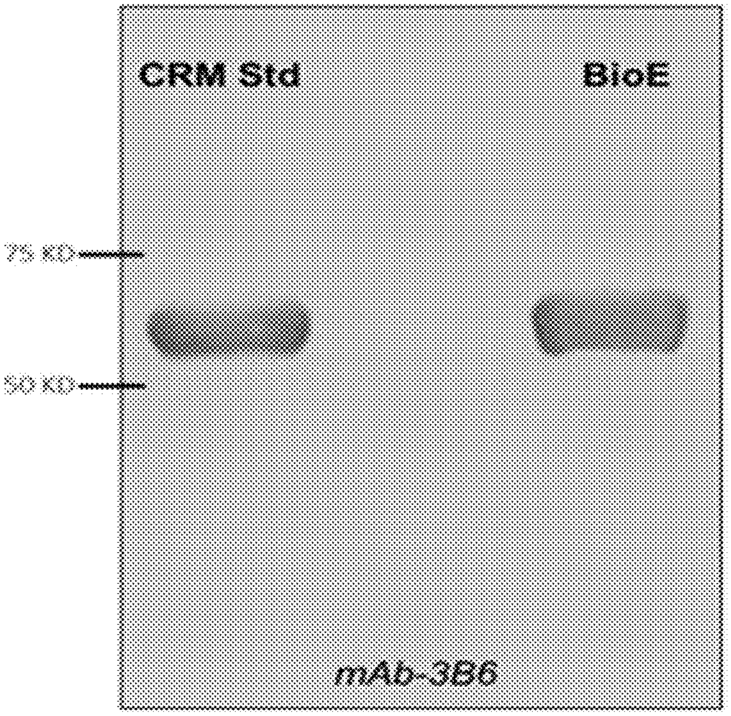
FIG. 5: Western Blot of purified $CRM_{197}$ wherein Lane 1 loaded with Std $CRM_{197}$ and lane 3 loaded with $rCRM_{197}$.
Figure 6:
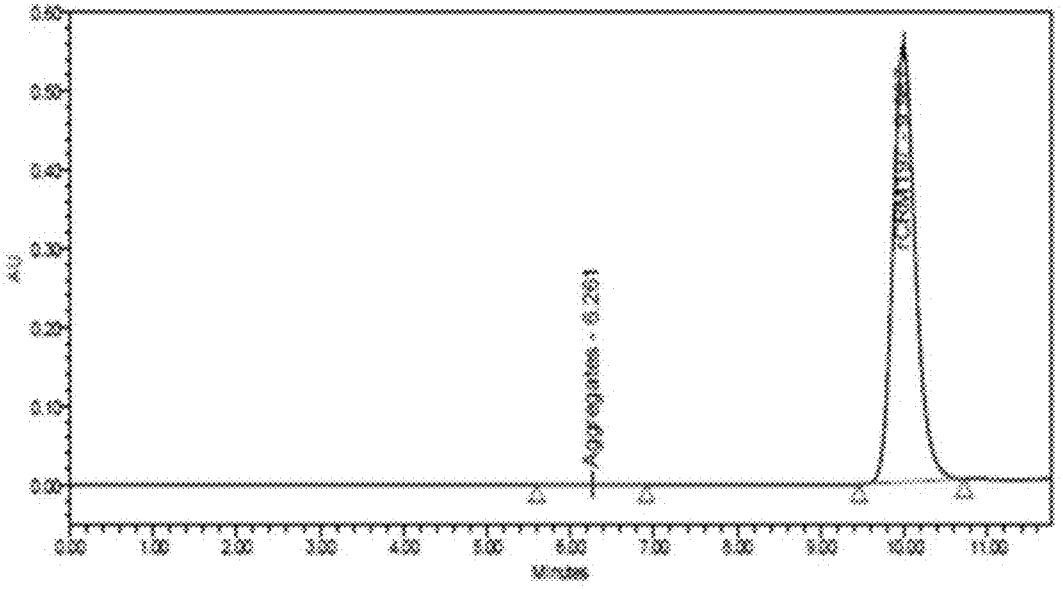
FIG. 6: SEC—HPLC chromatogram of purified $CRM_{197}$ wherein X-axis represents retention time (min) and Y-axis milli absorbance unit (mAU) at 280 nm.

| S. No. | Description | Specifications |
|---|---|---|
| 1 | Identity | Western blot: a major immunoreactive band of mass 58 kD ± 10%(FIG. 5) |
| 2 | Purity | SDS PAGE; $CRM_{197}$ NLT 90%(FIG. 4) |
| 3 | Nicked CRM (A and B Chain) | SDS PAGE: Reducing gel Commassie Blue; A and B chain content NMT 10% (total) of total $CRM_{197}$(FIG. 4) |
| 4 | Dimer/higher mol. Weight SEC - HPLC | NMT 15% (FIG. 6) |
| 5 | Endotoxin | NMT 100 EU/100 ug |

In yet another embodiment of the invention, purification by chromatography is carried out using single or multi step chromatography selected from i) direct ion exchange followed by ion exchange followed by hydrophobic interaction chromatography and ii) Ion exchange followed by hydrophobic interaction chromatography (HIC). Further the said ion exchange chromatography is an anion exchange chromatography. The anion exchange resins are selected from the group but not limited to consisting of DEAE cellulose, MonoQ, Capto Q, Eshmino Q, Gigacap Q 650M, Nuvia-Q, Cellufine Q-h, MiniQ, Source 15Q and 30Q, Q, DEAE Sepharose Fast Flow, Q Sepharose high Performance, QAE SEPHADEX™ and FAST Q SEPHAROSE™ (GE Healthcare), UNOsphere Q, Macro-Prep DEAE and Macro-Prep High Q from Biorad, Ceramic HyperD Q, ceramic HyperD DEAE, Toyopearl SuperQ-650S, 650M and 650C, QAE-550C and 650S, DEAE-650M and the like.

The anion exchange column is eluted at 10 to 60% of 1M NaCl in Tris-HCl buffer and the concentration of the buffer may range from 10 mM to 300 mM. The anion exchange column runs in the pH range of 6 to 9, preferably 8 to 9.

The hydrophobic interaction chromatography support is selected from the group but not limited to butyl-, phenyl-, octyl-agarose, butyl-, phenyl-, ether-organic polymer resin and phenyl sepharose and the like.

The hydrophobic interaction chromatography column runs in the pH range of 5 to 8, preferably 6 to 7.6.

The buffer used for hydrophobic interaction chromatography may be sodium or potassium phosphate containing sodium chloride ranging from 2M to 5M concentration or only sodium sulphate salt from 2M to 3M concentration.

In the specific embodiment, the carrier protein is $CRM_{197}$ and the yield of soluble $CRM_{197}$ is about 0.01 g/1, 0.1 g/1, 0.25 g/L, 0.5 g/L, about 1 g/L, about 1.5 g/L, about 2 g/L, about 2.5 g/L, about 3 g/L, about 3.5 g/L, about 4 g/L, about 4.5 g/L, about 4.5 g/L, about 5 g/L.

In another specific embodiment, the carrier protein is $CRM_{197}$ and the yield of insoluble $CRM_{197}$ is about 0.1 g/1, 0.25 g/L, 0.5 g/L, about 1 g/L, about 1.5 g/L, about 2 g/L, about 2.5 g/L, about 3 g/L, about 3.5 g/L, about 4 g/L, about 4.5 g/L, about 4.5 g/L, about 5 g/L.

The invention thus involves more than one subsequent purification steps, and also exploits pI value of $CRM_{197}$ in an ion exchange chroPmatographic step, whereby it is separated from other contaminating proteins. Finally, the quantity of $CRM_{197}$ was quantified by BCA/Bradford/Lowry Assay and visualised in 10-12% acrylamide gel (SDS-PAGE). The identification of polypeptide is done by Western blot and similar immunoassays. The purity and integrity of purified polypeptide is measured by SDS-PAGE and HPLC methods. The yield of the protein thus expressed was 500-3000 mg/L of the culture medium and can be subsequently varied by modulating the culture additives and conditions, as well as purification steps. The method of invention provides an industrially applicable method of tuning the induction time and subsequently modulating the pH and temperature of the chromatographic steps provides simple, inexpensive, and is not laborious. It excludes need of extensive steps involving preparation of buffers or kit or working solution thereof.

In the particular embodiment the purified $CRM_{197}$ polypeptide readily lacked the first Met amino acid, whose presence is not desired in the final $CRM_{197}$ protein and removal of which entails requirement for additional purification steps. The polypeptide thus obtained is in active and native form; it readily lacks the undesired methionine as first amino acid without the need of additional steps. $CRM_{197}$ amino acid sequence was analyzed by Insilico/bioinformatics tools; showed about 38.4% hydrophobicity in the protein. The isoelectric point of $CRM_{197}$ was found about 5.81. $CRM_{197}$ protein contained 4 cysteine amino acid residue and 21 proline residues. The refolding of polypeptide is confirmed by functional assays by measuring endonuclease activity over DNA. Biophysical confirmation was done by Circular Dichroism (CD) analysis of polypeptide and compared with commercially available polypeptides.

The carrier proteins prepared according to the present invention is used to conjugate with polysaccharide molecules isolated from Pneumococcus *Haemophilus influenzae, Meningococcus, Streptococcus pneumoniae* and other pathogenic bacteria.

In another embodiment, the carrier proteins prepared according to the present invention is used as a conjugated carrier for vaccines such as those against Pneumococcus *Haemophilus influenzae, Meningococcus, Streptococcus pneumoniae* and other pathogenic bacteria.

The process of the present invention does not require chaotropic agents nor refolding buffers (classical dilution based methods), which makes the process simple and commercially feasible.

A very high amount and pure form of carrier proteins can be achieved by the process disclosed and illustrated herein.

Carrier proteins prepared according to the process of the present invention are economical and requires less time.

The present invention is more specifically illustrated with reference to the examples given below. However, it should be understood that the present invention is not limited by an example in any manner but includes other carrier proteins and variations thereof within the parameters described herein, as can be known to those well-versed in the art.

Example I

Step (i): Synthesis of $CRM_{197}$ Gene:

Full length $CRM_{197}$ gene was optimized according to *Escherichia coli* codon usage. The following parameters were used for $CRM_{197}$ gene optimization: Codon Usage Bias, GC content, mRNA Secondary Structure, Custom Desired Patterns, Custom Undesired Patterns, Repeat Sequences (direct repeat, inverted repeat, and dyad repeat), Restriction Enzyme Recognition Sites (deletion or insertion).

Optimized $CRM_{197}$ gene was cloned at multiple cloning site of pUC57 plasmid vector using BamH1 and Sap1 restriction sites, generating pUC57_$CRM_{197}$. The vectors containing $CRM_{197}$ gene was transformed in *Escherichia coli* DH5a host and clones was selected on LB+Kanamycin$^r$ plate. The presence and correctness of $CRM_{197}$ gene in pUC57 was confirmed by restriction digestion of pUC57_$CRM_{197}$ plasmid by Age I (located in $CRM_{197}$ gene) and Nde I (located in pUC57 plasmid). Further the sequence of $CRM_{197}$ was confirmed by PCR and DNA sequencing.

Step (ii): Insertion of $CRM_{197}$ into Expression Vector pTWIN1

*Escherichia coli* DH5a carrying pUC57_$CRM_{197}$ was grown over night in LB+Kanamycin in 50 ml volume. Bacteria was centrifuged and pellet was used for plasmid isolation. Isolation of plasmid was done by using Qiagen plasmid mini-prep kit using manufacturer instructions. Isolated plasmid was quantified by nono-drop.

$CRM_{197}$ from pUC57 was excised, 5 μg plasmid was digested with restriction endonucleases BamHI and SapI. The digested plasmid was run on 1% agarose gel and band corresponding to $CRM_{197}$ gene was purified by using Qiagen Gel extraction kit using manufacturer's instructions. Subsequently the 5 μg of expression plasmid pTWIN1 was also digested with BamHI and SapI to generate restriction sites in it that is compatible with $CRM_{197}$ gene. The digested pTWIN1 was also purified from gel using Qiagen Gel extraction kit with manufacturer's instructions.

The digested $CRM_{197}$ gene was ligated in pTWIN1 using T4 ligase based DNA ligation kit (Promega) using manufacturer's instructions. Vector (pTWIN1) and Insert ($CRM_{197}$) was mixed in 1:3, 1:4, 1:5 ratio in the presence of T4 DNA ligase and buffers in a 20 μl reaction volume. Ligation mixture was incubated overnight at 16° C. Next morning 5 μl of ligation mixture was added/transformed in BL21-DE3 *Escherichia coli* expression host. BL21 was transformed by using chemical transformation protocol. The ligation+BL21 cells were incubated in ice for 30 min. After incubation heat shock was given for 45 seconds at 42° C. Sample was cooled at room temperature and 500 μl SOC medium was added into it. The tube with transformants was incubated for 2 hours at 37° C. with 200 rpm. From which 100 μl mixture was plated on LB+Ampicillin plate for screening of transformants.

$CRM_{197}$ expression BL21-DE3 transformants were selected next morning from Luria Broth+Ampicillin plates. Of these 5 clones growing on Luria Broth+Ampicillin were selected and grown in 10 ml Luria Broth+Ampicillin media for overnight at 37° C., 200 rpm. Culture was centrifuged and plasmid was extracted from cell pellet using Qiagen plasmid extraction kit.

To verify the correctness of clone, 2 μg plasmid was digested with AgeI and ApaI restriction endonuclease, respectively. AgeI site is present in $CRM_{197}$ and ApaI is in pTWIN1. Therefore double digestion with both the enzymes used for confirmation of correct clone. The clone was designated as pTWIN1_$CRM_{197}$ (BL21-DE3). Furthermore clones were confirmed by PCR using $CRM_{197}$ gene specific primers and DNA sequencing. The glycerol stock of BL21 expressing $CRM_{197}$ was made by growing bacteria in 10 ml Luria Broth+Ampicillin overnight. Next morning 40% sterilized Glycerol was added into culture and 1 ml aliquot was dispensed into cryovial. Vials were stored at −80° C. for further use in expression analysis.

Figure 2:
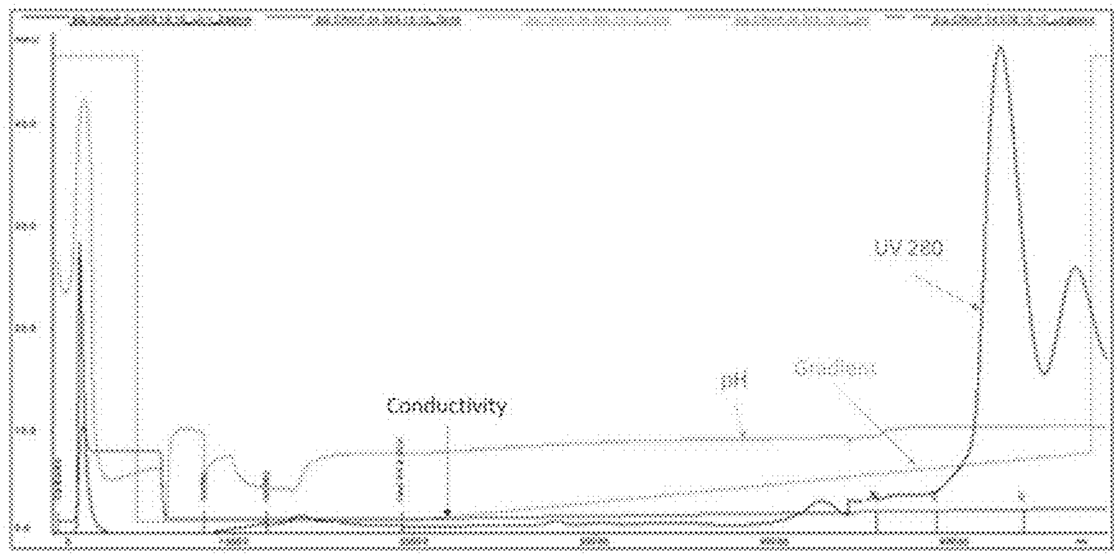
FIG. 2: Ion Exchange chromatogram elute from first chromatography is concentrated and diafiltered. This protein sample was loaded on second anion exchange resin at the flow rate of 150-300 cm per hour. Flow—through and equilibration wash consists of low molecular weight impurities and other remaining cellular impurities. Linear gradient elution is performed to recover rCRM from fusion protein followed by column regeneration. This chromatography is used as intermediate purification chromatography. Wherein Y-axis represents absorbance at 280 (mAU) and X-axis represents retention volume (ml).

Step (iii): Confirmation of Expression of $CRM_{197}$:

BL21 clone stored at −80° C. was streaked on Luria Broth+Ampicillin plate. Plate was incubated overnight at 37° C. Single colony was picked up and inoculated in 50 ml Luria Broth+Ampicillin media in 150 ml flask. Flask was incubated at 37° C., 200 RPM until OD600=1. Once OD reaches to desired point, 5 ml culture was drawn which is used as uninduced culture. Uninduced culture was kept on ice until use. To induce the expression of $CRM_{197}$ gene 0.5 mM IPTG was added to remaining 45 ml culture and flask was further incubated for additional 4 hours at 30° C. and 200 rpm rotation. Induced culture was harvested after 4 hours and expression of $CRM_{197}$ was examined by SDS-PAGE (FIG. 1) and Western Blot (FIG. 2).

For SDS-PAGE analysis 1 ml culture of induced and uninduced culture (both normalized for OD600=1) was taken into 1.5 ml Eppendorf tube. The tube was centrifuged and pellet was resuspended into 50 μl PBS. In this suspension 50 μl SDS-PAGE loading buffer with reducing agent (2×) was added. The mixture was boiled at 100° C. for 5 min. Sample was cooled at room temperature and 20 μl of uninduced and induced culture was loaded in the 4-12% Tris Glycine gel. The gel was run for 1.5 hours at 150 volts. Gels were taken out and incubated in Coomassie Brilliant Blue dye for 1 hour. After staining gel was detained in destaining solution containing 40% methanol=10% acetic acid for 3 hours. The $CRM_{197}$ expression was visualized as ~58 KD protein that is only visible in induced culture. For western blot a separate set of gel was run in the same manner as SDS-PAGE and gel was blotted on PVDF (polyvinylidene difluoride membrane). The membrane was immunoblotted by anti-$CRM_{197}$ antibody. In the western blot $CRM_{197}$ appeared as single immunoreactive band at ~58 Kd. No $CRM_{197}$ specific band was observed in uninduced culture. This experiment confirms that the clone generated in the present study can express r$CRM_{197}$ protein. These clone were further used for large scale production and purification of $CRM_{197}$.

Step (iv): Inclusion Bodies Preparation

One ml vial of BL21 *Escherichia coli* cells was inoculated into 50 ml LB+Amp media and grown overnight at 37° C., 200 rpm. Fermentation was done at 20 L scale. *Escherichia coli* cells were inoculated to the fermenter and cultivated at 30° C. centigrade. The culture was induced with 0.5 mM IPTG at OD600=20. After 12 hours post induction fermentation culture was harvested and cell pellet was prepared by centrifugation. Cell pellet was lysed mechanically in homogenizer. Inclusion body (which contains the desired protein $CRM_{197}$) was isolated by centrifugation of cell lysates. Supernatant was discarded and pellet was retained which contains Inclusion body (IBs). The isolated inclusion bodies are purified using three wash buffers wherein first containing 20 mM Tris+250 mM NaCl, second containing 20 mM Tris+2M Urea+1% Triton X-100 and third one containing 20 mM Tris to obtain purified rCRM inclusion bodies.

Example II 100 g $CRM_{197}$ protein inclusion bodies were denatured by high pH, dissolved by stirring at 120 min, clarified by centrifugation for 40 minutes, the supernatant was collected and further clarified by 0.8-0.45μ filter. Wherein said denaturing solution contained 100 mM Tris-, pH 12.0. Refolding was performed by adjusting pH to 8 using 100-250 mM HCl containing 10 mM Cysteine, 20 mM Cysteine pH 2.0 without any dilution by passing through static mixer (Sulzer and Koflow are the two manufacturers of in-line static mixer) for <10 milli seconds.

Anion exchange column (Capto Q, first anion exchange step) equilibrated with 50 mM Tris-HCl, pH8.0 buffer contacted with refolded protein solution, followed by elution with 20-50 mM NaCl in 50 mM Tris-HCl, pH8.0 buffer.

The protein elute subjected to 10 kDa UF/DF (1$^{st}$ UF/DF) step to remove salt and concentrate the protein solution.

The above concentrated and diafiltered protein elute contacted with second anion exchange column (Source 30Q) equilibrated with 50 mM Tris-HCl, pH8.0 buffer, followed by linear gradient elution with 10-15 mM NaCl in 50 mM Tris-HCl, pH8.0 buffer.

The protein elute subjected to 10 kDa UF/DF (2$^{nd}$ UF/DF) step to remove salt and concentrate the protein solution.

The above concentrated and diafiltered protein elute toned with 3M NaCl by adding calculated solid NaCl and contacted with hydrophobic interaction column (Phenyl Sepharose FF) equilibrated with 50 mM Tris-HCl, 3M NaCl pH8.0 buffer, followed by elution with 10 mM potassium phosphate, pH7.2 buffer.

The protein elute subjected to 10 kDa UF/DF (1$^{st}$ UF/DF) step to remove salt and concentrate the protein solution. The protein solution is diafiltered with 10 mM potassium phosphate, 5% sucrose pH7.2 buffer.

The concentrated and diafiltered protein elute filtered through 0.22μ filtered and frozen at −70° C.

Figure 3:
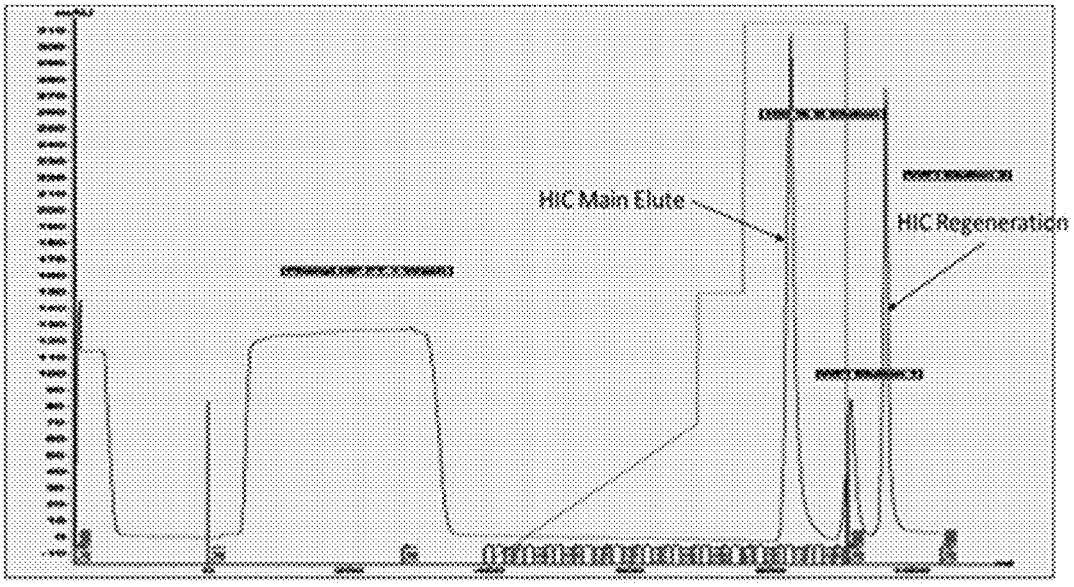
FIG. 3: HIC chromatogram elute from second chromatography is concentrated and diafiltered. This protein sample was loaded on hydrophobic interaction resin at the flow rate of 150-300 cm per hour. Flow—through and equilibration wash consists of endotoxins, host cell nucleic acids and remaining cellular impurities. Gradient elution step is performed to recover rCRM followed by column regeneration. This chromatography is used as polishing chromatography wherein Y-axis represents absorbance at 280 (mAU) and X-axis represents retention volume (ml).

Intermediate purification of the refolded protein (FIG. 1) using ion exchange chromatography is carried out to obtain >90% pure and native carrier protein and the semi purified protein obtained as a result of intermediate purification is subjected to further chromatographic separation (FIGS. 2 and 3) to obtain purified carrier proteins Impact of mixing time on pH was evaluated for refolding of $rCRM_{197}$. The pH based refolding was performed at 4° C., the dilution ratio was kept constant. The mixing time was changed from 2000 milli seconds to 60 milli seconds using inline static mixer. Table II shows the impact of reduction in mixing time is directly proportional to % rCRM refolding.

TABLE II

Figure 7:
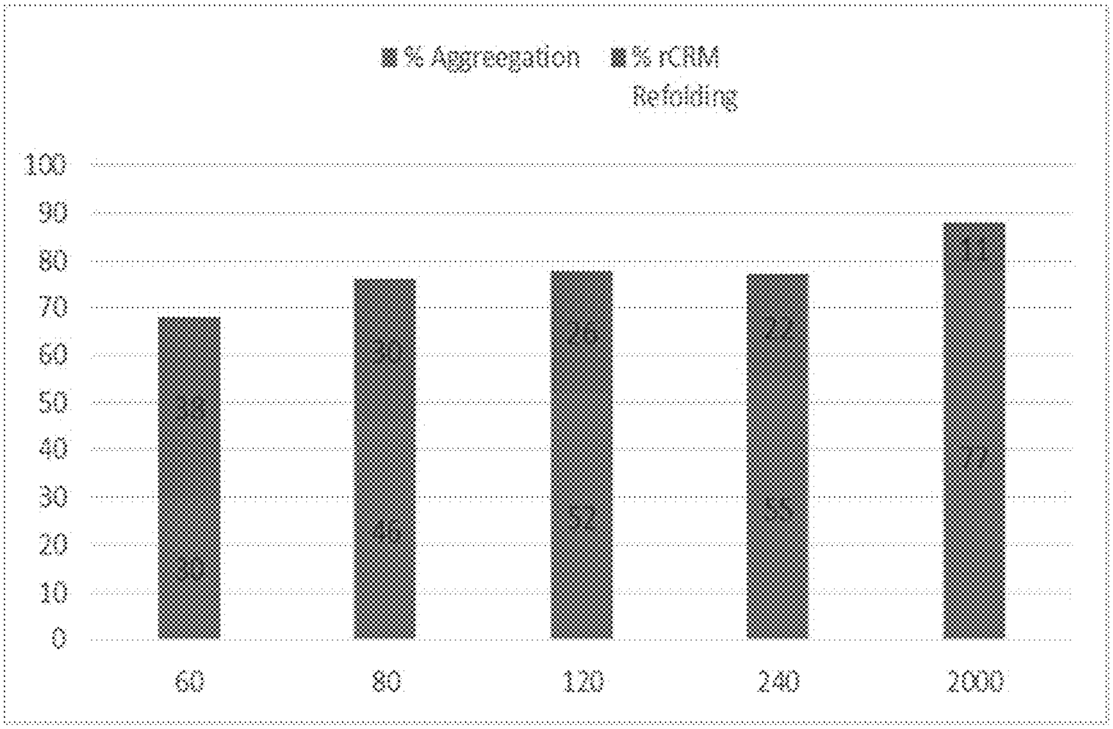
FIG. 7: Impact of inline mixing on refolding of $rCRM_{197}$. Y-axis represents % refolding & % aggregation and X-axis represents time in milliseconds.

Impact of inline mixing on refolding of $rCRM_{197}$. (FIG. 7)

| S. No. | Dilution Fold | Mixing Time (milli seconds) | % Aggregation | % rCRM Refolding |
|---|---|---|---|---|
| 1 | 1.5x | 60 | 30 | 38 |
| 2 | 1.5x | 80 | 46 | 30 |
| 3 | 1.5x | 120 | 52 | 26 |
| 4 | 1.5x | 240 | 55 | 22 |
| 5 | Traditional mixing | 2000 | 77 | 11 |

Refolding parameters of the $CRM_{197}$ prepared according to above described procedure is compared with the $CRM_{197}$ prepared according to the conventional refolding process described herein.

Inclusion body based proteins are solubilized using chaotropic salts. The refolding is performed by lowering the concentration of the chaotropic salt, this is achieved by dilution (over 100 fold). The dilution results in lowering the protein concentrations below 200 microgram/ml. The conventional dilution based refolding is not feasible in large scale manufacturing due to requirement of very large scale refolding vessels.

Comparison of the conventional refolding process with the process of the present invention is laid in Table III below.

TABLE III

| Parameters | Conventional Refolding Process | Process of the present Invention |
|---|---|---|
| Target Protein conc (mg/ml) | ~0.2 | ~5 |
| Dilution required | ~40X | ~1.5X |
| Refolding Volume | ~40 L | ~1.5 L |
| Facility requirement | High volume vessels | Low volumes |
| Further process time | very high | Minimal process time |

Various batches of $CRM_{197}$ with similar conditions described in the Example 2 have been prepared. The yield of $CRM_{197}$ obtained from 3 different batches. The data disclosed in Table IV indicates the consistency in the refolding.

TABLE IV

Yield of rCRM197

| Batch No. | Inclusion body $rCRM_{197}$content (mg/L) | % Refolding | Refolded & purifiedr$CRM_{197}$ Productivity (mg/L) |
|---|---|---|---|
| TD/CRM/CRM-P/012-002/15 | 2400 | 19.4 | 340 |
| TD/CRM/CRM-P/013-004/15 | 2200 | 17.49 | 347 |
| TD/CRM/CRM-P/013-005/15 | 2900 | 18.2 | 342 |

The invention claimed is:

1. An industrially scalable method for preparation of carrier proteins selected from tetanus toxoid (TT), diphtheria toxoid (DT), Cross Reactive Material 197 ($CRM_{197}$), *Haemophilus influenzae* protein D, *Neisseria* outer membrane protein, Pertussis toxin (PT), Pertactin (PRN), and Filamentous Hemagglutinin (FHA), the method comprising the steps of:

a) transformation of *Escherichia coli* with a desired gene coding for the carrier protein using a plasmid vector, b) culturing the transformed *Escherichia coli* in suitable culture medium under suitable conditions, c) isolation and purification of inclusion bodies, d) denaturation and solubilization of inclusion bodies at high pH value ranging from 9 to 14, e) followed by pH adjustment within a range of 6 to 8.5, preferably at 8 of the solubilized protein using in-line static mixer for a period of 0.1 to 200 msec, to produce a refolded protein, f) intermediate purification of the refolded protein using ion exchange chromatography to obtain >90% pure native carrier protein and g) the semi purified protein obtained in step (f) is further purified by one or more chromatographic separation using anion exchange chromatography, hydrophobic interaction chromatography, metal & dye affinity chromatography, affinity chromatography, multimodal chromatography, hydroxyapatite chromatography and size exclusion chromatography to obtain the carrier protein.

2. The industrially scalable method for preparation of carrier proteins of claim 1, wherein the refolding step has been optimized using in-line static mixer by rapid pH adjustment within a range of 6 to 8.5, preferably at 8 for a period of 1 to 200 microseconds.

3. The industrially scalable method of claim 1, wherein the method does not involve use of refolding buffers and is optimized using in-line static mixer by rapid pH adjustment within a range of 6 to 8.5, preferably at 8 for a period of 10 to 200 microseconds.

4. The industrially scalable method of claim 1, wherein the solubilization of inclusion bodies is carried out at high pH value ranging from 9 to 14 without use of chaotropic agent.

5. An industrially scalable method for preparation of Cross Reactive Material 197 ($CRM_{197}$), the method comprising the steps of:

a) transformation of *Escherichia coli* with a gene coding for $CRM_{197}$ using a plasmid vector, b) culturing the transformed *Escherichia coli* in suitable culture medium under suitable conditions, c) isolation and purification of inclusion bodies, d) denaturation and solubilization of inclusion bodies at high pH value ranging from 9 to 14, e) followed by pH adjustment within a range of 6 to 8.5, preferably at 8 of the solubilized protein using in-line static mixer for a period of 0.1 to 200 msec, to produce refolded protein, f) intermediate purification of the refolded protein using ion exchange chromatography to obtain >90% pure native $CRM_{197}$ and g) the semi purified $CRM_{197}$ obtained in step (f) is further purified by one or more chromatographic separation using anion exchange chromatography, hydrophobic interaction chromatography, metal & dye affinity chromatography, affinity chromatography, multimodal chromatography, hydroxyapatite chromatography and size exclusion chromatography to obtain $CRM_{197}$.

6. The industrially scalable method of claim 5, wherein the refolding step is optimized using in-line static mixer by rapid pH adjustment within a range of 6 to 8.5, preferably at 8 for a period of 1 to 200 microseconds.

7. The industrially scalable method of claim 5, wherein the industrially scalable method does not involve use of refolding buffers and is optimized using in-line static mixer by rapid pH adjustment within a range of 6 to 8.5, preferably at 8 for a period of 10 to 200 microseconds.

8. The industrially scalable method of claim 5, wherein the solubilization of inclusion bodies is carried out at high pH value ranging from 9 to 14 without the use of chaotropic agent.

9. The industrially scalable method of any one of claims 1 to 8, wherein a yield of insoluble $CRM_{197}$ is from about 0.01 to 5 g/l.

10. The industrially scalable method of any one of claims 1 to 8, wherein a yield of soluble $CRM_{197}$ is from about 0.01 to 5 g/l.

11. A process for preparation of recombinant carrier proteins selected from tetanus toxoid (TT), diphtheria toxoid (DT), Cross Reactive Material 197 ($CRM_{197}$), *Haemophilus influenzae* protein D, *Neisseria* outer membrane protein, Pertussis toxin (PT), Pertactin (PRN) and Filamentous Hemagglutinin (FHA) from a prokaryotic expression system, wherein protein is expressed as inclusion bodies which comprises:

a. transformation of bacterial cells with a desired gene coding for carrier proteins using a plasmid vector, b. culturing the transformed bacterial cells in chemically defined media supplemented with glucose as carbon source wherein pH is maintained at 5-9 and at temperature of 20-40° C.;

c. lysing bacterial cells by mechanical means above 800-1200 bars thereby producing a lysate containing inclusion bodies and cellular components;

d. clarifying the cell lysate by separating solids from the solution;

e. isolation and purification of inclusion bodies (IBs) by using buffers selected from carbonate, bicarbonate, Tris, borate, Glycine and NaOH to remove cellular contaminants to form a pellet of purified IBs;

f. denaturation and solubilisation of (IBs) at a high pH value ranging from 9 to 14 using at least one buffer selected from carbonate, bicarbonate, Tris, borate, Glycine and NaOH buffer;

g. rapid pH adjustment within a range of 6 to 8.5, preferably at 8 of solubilized carrier proteins using acid containing redox systems and inline static mixer for a period of 0.1 to 200 msec, to produce refolded protein, h. intermediate purification of the refolded protein using ion exchange chromatography to obtain >90% pure native carrier protein and i. the semi purified protein obtained in step (h) is further purified by one or more chromatographic separations using anion exchange chromatography, hydrophobic interaction chromatography, metal & dye affinity chromatography, affinity chromatography, multimodal chromatography, hydroxyapatite chromatography and size exclusion chromatography to obtain to obtain carrier protein.

* * * * *